(12) United States Patent
Korb et al.

(10) Patent No.: US 9,459,370 B2
(45) Date of Patent: Oct. 4, 2016

(54) METHOD OF DETERMINING FORMATION PARAMETER

(75) Inventors: Jean-pierre Korb, Palaiseau (FR);
Gabriel Freiman, Palaiseau (FR);
Benjamin Nicot, Dammam (SA);
Patrice Ligneul, Chaville (FR)

(73) Assignee: SCLUMBERGER TECHNOLOGY CORPORATION, Cambridge, MA (US)

( * ) Notice: Subject to any disclaimer, the term of this patent is extended or adjusted under 35 U.S.C. 154(b) by 792 days.

(21) Appl. No.: 12/993,681

(22) PCT Filed: Jul. 7, 2009

(86) PCT No.: PCT/US2009/049810
§ 371 (c)(1),
(2), (4) Date: Apr. 14, 2011

(87) PCT Pub. No.: WO2010/005967
PCT Pub. Date: Jan. 14, 2010

(65) Prior Publication Data
US 2011/0181277 A1    Jul. 28, 2011

(30) Foreign Application Priority Data

Jul. 8, 2008  (EP) ..................... 08290674

(51) Int. Cl.
*G01V 3/32*    (2006.01)
*G01V 3/00*    (2006.01)
*G01N 24/08*   (2006.01)
*G01R 33/44*   (2006.01)

(52) U.S. Cl.
CPC .................. *G01V 3/32* (2013.01); *G01N 24/08* (2013.01); *G01N 24/081* (2013.01); *G01R 33/445* (2013.01); *G01R 33/448* (2013.01)

(58) Field of Classification Search
CPC ...... G01V 3/32; G01N 24/081; G01N 24/08; G01R 33/445; G01R 33/448
USPC ......................................................... 324/303
See application file for complete search history.

(56) References Cited

U.S. PATENT DOCUMENTS

| | | | |
|---|---|---|---|
| 5,023,551 A * | 6/1991 | Kleinberg et al. | 324/303 |
| 6,765,380 B2 | 7/2004 | Freedman et al. | |
| 6,883,702 B2 | 4/2005 | Hurlimann et al. | |

(Continued)

OTHER PUBLICATIONS

Godefroy Set Al: "Surface nuclear magnetic relaxation and dynamics of water and oil in macroporous media" Physical Review E, vol. 64, No. 2, Aug. 1, 2001, pp. 21605/1-21605/13, XP007906283 ISSN: 1063-651X.*

(Continued)

*Primary Examiner* — Melissa Koval
*Assistant Examiner* — Rishi Patel
(74) *Attorney, Agent, or Firm* — Bridget M. Laffey; Jakub Michna

(57) ABSTRACT

A nuclear magnetic resonance relaxation dispersion method to determine the wettability and other parameters of a fluid in a porous medium such as in an earth formation is provided. The method includes the steps of measuring the spin-lattice relaxation time $T_1$ of the fluid in the porous medium at varying polarizing magnetic field strengths or nuclear Larmor frequencies; and determining whether the values of $T_1$ at varying Larmor frequencies follow a dispersion curve that is characteristic of the parameter of the fluid in the porous medium to be determined.

9 Claims, 9 Drawing Sheets

(56) References Cited

U.S. PATENT DOCUMENTS

| 2003/0169040 A1* | 9/2003 | Hurlimann et al. ......... 324/303 |
| 2004/0000905 A1* | 1/2004 | Freedman et al. ........... 324/303 |
| 2004/0008027 A1* | 1/2004 | Prammer ................ G01V 3/32 324/303 |
| 2006/0132131 A1* | 6/2006 | Fleury et al. ................ 324/307 |

OTHER PUBLICATIONS

Mattea C et al: "Molecular exchange dynamics in partially filled microscale and nanoscale pores of silica glasses studied by field-cycling nuclear magnetic resonance relaxometry" Journal of Chemical Physics, vol. 121, No. 21, Dec. 1, 2004, pp. 10648-10656, XP009108702 ISSN: 0021-9606.*

Stapf et al.: "Proton and Deuteron Field-Cycling NMR Relaxometry of Liquids in Porous Glasses: Evidence for Lévy-Walk Statistics" Physical Review Letters, vol. 75, No. 15, Oct. 9, 1995, pp. 2855-2858, XP002504332.*

Korb J-P et al: "Anomalous surface diffusion of water compared to aprotic liquids in nanopores" Physical Review E, vol. 60, No. 3, Sep. 1, 1999, pp. 3097-3106, XP007906282 ISSN: 1063-651X.*

Korb J-P et al: "Translational diffusion of liquids at surfaces of microporous materials: Theoretical analysis of field-cycling magnetic relaxation measurements" Physical Review E, vol. 56, No. 2, Aug. 1, 1997, pp. 1934-1945, XP007906279 ISSN: 1063-651X.*

EPO Action; Dec. 11, 2008; EPO; pp. 1-13.*

Plassais et al. "Microstructure evolution of hydrated cement pastes," Oct. 5, 2005; Pysical Review E 72, 041401.*

Bloembergen, et al., "Proton Relaxation Times in Paramagnetic Solutions. Effects of Electron Spin Relaxation", Journal of Chemical Physics, vol. 34(3), 1961, 9 pages.

Depavia, et al., "A Next-Generation Wireline NMR Logging Tool", SPE 84482, SPE Annual Technical Conference and Exhibition, Denver Colorado, Oct. 5-8, 2003, 7 pages.

Godefroy, et al., "Temperature Effect on NMR Surface Relaxation in Rocks for Well Logging Applications", Journal of Physical Chemistry B, vol. 106(43), 2002, pp. 11183-11190.

Korb, et al., "Paramagnetic relaxation of protons in rotationally immobilized proteins", Journal of Chemical Physics, vol. 124, 2006, pp. 1-6.

Korb, et al., "Surface dynamics of liquids in porous media", Magnetic Resonance Imaging, vol. 19(3-4), Apr. 1, 2001, pp. 363-368.

Meiboom, et al., "Modified SpinEcho Method for Measuring Nuclear Relaxation Times", Review of Scientific Instruments, vol. 29, 1958, pp. 688-691.

International Search Report issued in PCT/US2009/049810 on Aug. 10, 2009, 7 pages.

Written Opinion issued in PCT/US2009/049810 on Aug. 10, 2009, 16 pages.

\* cited by examiner

METHOD OF DETERMINING FORMATION PARAMETER

FIELD OF THE INVENTION

This invention relates to investigations of porous media, more particularly to nuclear magnetic relaxation (NMR) methods and apparatus for determining the wettability and other parameters of such media.

BACKGROUND

Nuclear magnetic relaxation methods offer a variety of opportunities for characterizing the molecular dynamics in confined environments. Systems of interest are high surface area materials including biological tissues, chromatographic supports, heterogeneous catalytic materials and natural porous materials such as clay minerals and rocks.

Nuclear magnetic relaxation dispersion (NMRD) consists in measuring the observables of relaxation as a function of the magnetic field. It enlarges drastically the timescale and lengthscale of observation of the molecular dynamics especially in porous media.

NMR has been a common laboratory technique for over forty years and has become an important tool in formation evaluation. General background of NMR well logging can be found, for example, in U.S. Pat. No. 5,023,551 to Kleinberg et al., which is assigned to the same assignee as the present invention and herein incorporated by reference in its entirety.

NMR relies upon the fact that the nuclei of many chemical elements have intrinsic angular momentum ("spin") and a magnetic moment. In an externally applied static magnetic field, the spins of nuclei align themselves along the direction of the static field. This equilibrium situation can be disturbed by a pulse of an oscillating magnetic field (e. g., a radio frequency (rf) pulse) that tips the spins away from the static field direction. The angle through which the spins are tipped is given by $\theta = \gamma * B_1 t_P$, where $\gamma$ is the gyromagnetic ratio, $B_1$ is the linearly polarized oscillating field strength, and $t_P$ is the duration of the pulse. Tipping pulses of 90 and 180 degrees are most common.

After tipping, two things occur simultaneously. First, the spins precess around the direction of the static field at the Larmor frequency, given by $\omega_0 = \gamma * B_0$, where $B_0$ is the strength of the static field and $\gamma$ is the gyromagnetic ratio. For hydrogen nuclei, $\gamma/2\Pi$ equals 4258 Hz/Gauss. Secondly, the spins return to the equilibrium direction according to a decay time, $T_1$, which is known as the spin-lattice or longitudinal relaxation time.

Also associated with the spin of molecular nuclei is a second relaxation time, $T_2$, called the spin-spin or transverse relaxation time. At the end of a 90-degree tipping pulse, all the spins are pointed in a common direction perpendicular, or transverse, to the static field, and precess at the Larmor frequency. However, due to small fluctuations in the static field induced by other spins or paramagnetic impurities, the spins precess at slightly different frequencies, so that the transverse magnetization dephases with a relaxation time constant $T_2$.

Most NMR logging operations measure the spin-lattice (longitudinal) relaxation times ($T_1$) and/or spin-spin (transverse) relaxation times ($T_2$) of hydrogen nuclei. In addition, some NMR logging tools may provide a ratio of $T_1/T_2$ directly, and other NMR tools can provide diffusion constants (D) and combined D-$T_2$ plots.

Various pulse sequences are available for measuring the NMR relaxation times. For example, $T_1$ relaxation may be measured using an inversion-recovery or a simple spin-echo pulse sequence or any of their derivatives. The $T_2$ relaxation is often measured from a train of spin-echoes that are generated with a series of pulses such as the Carr-Purcell-Meiboom-Gill (CPMG) pulse sequence or some variant of this. The CPMG pulse sequence is well known in the art. (See Meiboom, S., Gill, D., 1958, "Modified Spin Echo Method for Measuring Nuclear Relaxation Times," Review of Scientific Instruments, 29, 688-91).

Wettability of oil/water liquids mixtures measured in porous rocks is one of the most critical parameters for oil recovery with porosity and permeability. Roughly, wettability is the ability of a fluid to spread over or "wet" a solid surface. It influences saturation, pore distribution and flow of fluids in porous materials. Nowadays, wettability is mainly measured by macroscopic measurements such as contact angles and capillary pressure curves (Amott and USBM methods).

Methods to determine the wettability of liquids in a porous media are described in various publications and patents. Among those patents are the co-owned U.S. Pat. No. 6,765,380 to Freedman et al., the co-owned U.S. Pat. No. 6,883,702 to Hurliman et al., and the published U.S. patent application 2006/0132131 to Fleury et al.

Studies relating to the frequency dispersion of the spin-lattice relaxation rate 1/T1 can be for example found in the references:

J.-P. Korb, M. Whaley-Hodges and R. G. Bryant, Phys. Rev. E, 56, 2, 1934-1945, (1997);

J.-P. Korb, M. Whaley-Hodges, Th. Gobron and R. G. Bryant, Phys. Rev. E, 60, 3, 3097-3106, (1999);

S. Godefroy, J.-P. Korb, M. Fleury and R. G. Bryant, Physical Review E, 64, 021605, (2001);

S. Godefroy, M. Fleury, F. Deflandre and J.-P. Korb, J. Phys. Chem. B, 106, 11183-11190, (2002) ; and J.-P. Korb, G. Diakova, R. G. Bryant, J. Chem. Phys. 124, 134910 (2006).

In the light of the prior art, it is an object of the invention to provide alternative methods for determining wettability and other parameters of a sample of a porous media. More specifically, it is seen as an object of the present invention to provide a quantitative in situ method for determining directly the wettability of liquids and other parameters of a sample of a porous media.

SUMMARY OF INVENTION

The present invention introduces a new method for determining the dynamical parameters of fluids embedded in various porous media. This method is based on nuclear magnetic relaxation dispersion (NMRD), the measurement of proton spin-lattice relaxation rates 1/T1 as a function of magnetic field strength or nuclear Larmor frequency.

In a preferred embodiment the method is used to determine the wettability of a porous media exploiting the very different relaxation features of the proton NMRD of oil and water in various cases of saturation, particularly for carbonate rocks of different porosities and permeabilities.

The benefit of exploring a very large range of low frequency is to isolate the typical dispersion features associated with the different processes of molecular surface dynamics. This allows an experimental separation of the surface and bulk microdynamics of oil and water even for a multiphasic saturation.

In a preferred embodiment, the invention includes the step of obtaining the saturation of phases in the media also obtained from this new method.

The preferred range of the Larmor frequency is 10 kHz to 20 MHz

In a further preferred embodiment of the invention a ratio of a surface residence time $\tau_s$ and a translational or diffusion correlation time $\tau_m$ or any parameter equivalent to said ratio is used to define a wettability index using for example the values of $A=\tau_s/\tau_m$ from 1 to infinity.

In a further preferred embodiment of the invention the existence of different dispersion curves in the signals are used to derive information relating to the pore size distribution in the porous medium.

In a further preferred embodiment of the invention the signals are obtained by a nuclear magnetic logging tool measuring signals at different radial distances from a wellbore, preferably from radial distances where the formation has an essentially equal saturation of the fluid.

Further details, examples and aspects of the invention will be described below referring to the following drawings.

DETAILED DESCRIPTION

Figure 1:
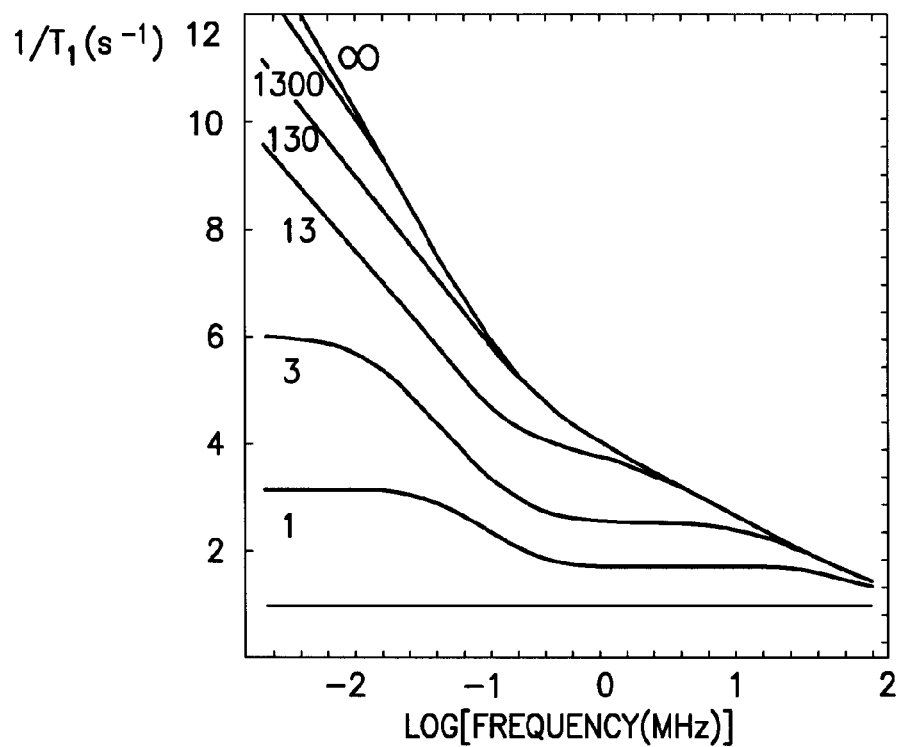
FIG. 1 shows theoretical plots of the frequency dependence of the proton relaxation rate $1/T_1$ for $\tau_m=1$ ns and varying the surface residence time Ts through the wettability index $A=\tau_s/\tau_m$ and with different parameter values in accordance with an example of the present invention.

The magnetic field dependence of the longitudinal nuclear spin relaxation rate $1/T_1$ (NMRD) is a rich source of dynamical information. Varying the magnetic field changes the Larmor frequency, and thus, the fluctuations to which the nuclear spin relaxation is sensitive.

The magnetic field dependence of the spin-lattice relaxation rate, $1/T_1$, provides a good test of the theories linking its measurement to the micro-dynamical behavior of the liquid. In confined systems, such as porous media, reduced dimensionality and Brownian diffusion may force more frequent reencounters between spin-bearing bulk molecules and concentrations of paramagnetic centers at the pore surface (like iron or manganese ions). This effect modifies the correlation functions in the relaxation equations in a fundamental way; the paramagnetic centers provide a large magnetic moment and local dipolar field in which the diffusing liquid spins move.

A paramagnetic site has an electronic spin creating a large magnetic moment unambiguously dominating the proton spin-lattice relaxation (the gyro-magnetic ratio of an electron $\gamma_s$ is 659 times greater than the gyro-magnetic ratio $\gamma_I$ of the proton).

In general, two classes of high surface area systems exists: solid phases that are proton-rich such as biological macromolecules including proteins, carbohydrates, and engineering polymers like polystyrene, and those that are proton-poor such as micro-porous glasses, zeolithes, clay minerals and rocks.

For the first class of high surface area systems cross-relaxation between the protons of the liquid and those of the solid may make dominant contributions to the nature of the magnetic field dependence of the nuclear spin relaxation rate observed.

For the second class of high surface area systems, the proton-poor solids, the two main effects dominate the liquid spin relaxation depend on the dynamical aspect of the molecular motion and the potential chemical exchange of protons at the solid surface. A protic traveling molecule (for instance water) can be trapped in the ligand field of a paramagnetic ion by a selective chemical binding whilst an aprotic traveling molecule (for instance alkane) may not be trapped to a paramagnetic ion but may stay close to the surface long enough to exhibit 2-Dimensional (2D) diffusion on the surface. As shown below, these physical-chemistry considerations of the proton spin-bearing molecules at a surface can be linked directly to wettability.

Based partly on prior art as expressed for example in the literature references cited above, two different ways of modeling the relaxation rates associated with protic and aprotic molecules are developed in the following. The first model applies to the case of protic or wetting molecules and the second model to aprotic or non-wetting molecules. The latter model includes also a parameter to describe the transition of the model from non-wetting to wetting behavior of the molecules.

For a non-wetting liquid, each traveling proton may not display affinity with the pore wall and thus will have a very short surface residence time $\tau_s$, i.e. close to the magnitude of the translational correlation time $\tau_m$, which in turn corresponds to the duration of an individual molecular jump at the surface. However for the correlation times it is still preferred to have $\tau_s/\tau_m>1$, as otherwise with $\tau_s/\tau_m=1$, the surface contribution as detailed by Eqs. [1] and [2] below tends to zero and the overall spin-lattice relaxation rate tends to the constant bulk term. For a low value of $A=\tau_s/\tau_m>1$ characteristic of a lack of dynamical affinity, one observes in a succession of plateau and slight relaxation decreases in the behavior of the nuclear magnetic spin-lattice relaxation dispersion (NMRD). So, when interpreted for example with a model based on Eq. [2] below, the NMRD provides a direct reliable value of surface diffusion coefficient, specific surface area and average pore size. The behavior of the NMRD under this condition is independent of the ligand properties of the paramagnetic sites.

For a wetting liquid, the proton spin-bearing molecule have the tendency to stay much longer in the proximity of the surface, leading to a much longer surface residence time $\tau_s$, thereby increasing the probability of the proton to be bound to a paramagnetic site.

In case the molecule is trapped in the ligand field of the paramagnetic site, its typical NMRD has a plateau at low frequency due to the electronic spin-lattice relaxation time $T_{1,param}$ and a peak at higher frequencies. This behavior can be for example observed in the well-known contrast agent for magnetic resonance imaging or MRI.

Even when the aprotic molecule is not trapped, it can still be expected to display a surface residence time $\tau_s$ much longer than the translational correlation time $\tau_m$. In this case, like in the non-wetting case described above, the liquids show a true bilogarithmic behavior of the nuclear magnetic spin-lattice relaxation dispersion (NMRD). However, in contrast to the non-wetting fluid the dynamical surface affinity parameter $A=\tau_s/\tau_m$ will now have a very high value, i.e. $A=\tau_s/\tau_m \gg 1$, which can be derived from the data.

The importance of the ratio A to distinguish between wetting and non-wetting molecules as shown in FIG. 1 can be used advantageously to derive a wettability index based on the values of $A=\tau_s/\tau_m$ varying from 1 to $\infty$ with the lower range of values being indicative of a non-wetting species and the higher of a wetting one.

The qualitative considerations presented above are in the following used in two different mathematical models, one of which models the bilogarithmic behavior of the nuclear magnetic spin-lattice relaxation dispersion (NMRD) for low and high values of A, while the second model can be applied to molecules trapped by paramagnetic sites.

The model of nuclear relaxation of a molecule undergoing 2-D diffusion close to a pore surface without being affected by a ligand field is hence applicable when the paramagnetic sites do not create a ligand field trapping a polar molecule, either because the fluid is non wetting (i.e. far from the paramagnetic site) or because the paramagnetic sites are not accessible, for example buried "far" from the pore surface or screened by another wetting fluid.

Moreover, the model of this example assumes that the limit of fast-diffusion where the biphasic fast exchange model between surface and bulk molecules is valid even in macro-porous media with a very small surface to volume ratio. The overall frequency dependency of the proton relaxation rate $1/T_1$ for this model can then be written as a linear combination of a bulk term $1/T_{1,bulk}$ and a frequency dependent surface term:

$$\frac{1}{T_1(\omega_I, \omega_S)} = \frac{1}{T_{1,bulk}} + \frac{N_{Surface}}{N} \frac{1}{T_{1,surface_I}(\omega_I, \omega_S)}, \quad [1]$$

where $N_s/N=\lambda*Ss/V$ is the ratio of number of liquid molecules in a surface layer of size $\lambda$ at proximity of the pore surface (FIG. 1a) and $\omega_I$ is the Larmor frequency of the proton and $\omega_s$ is the Larmor frequency of the electron. The bulk relaxation term $1/T_{1,bulk}$ is assumed in this model to be a constant with no frequency dependence in at least the low frequency range.

As detailed in the above cited references, the following quantitative expression can be applied to the case of a aprotic liquid embedded in pores:

$$\frac{1}{T_1(\omega_I)} = \frac{1}{T_{1,bulk}} + \frac{\pi}{20}(\lambda S_P \rho_{liquid}) \frac{(\eta_S \rho_{solid} \xi)}{\delta^4}(\gamma_I \gamma_S \hbar)^2 S(S+1) \quad [2]$$

$$\tau_m * \left[ 3\ln\left(\frac{1+\omega_I^2 \tau_m^2}{(\tau_m/\tau_S)^2 + \omega_I^2 \tau_m^2}\right) + 7\ln\left(\frac{1+\omega_S^2 \tau_m^2}{(\tau_m/\tau_S)^2 + \omega_S^2 \tau_m^2}\right) \right]$$

In equation [2] $S_p$ is the specific surface area of the solid rock, and $\rho_{solid}$ and $\rho_{liquid}$ are the densities of the rock and liquid, respectively. Substituting the surface to volume ratio with $S_p$ leads to $N_{Surface}/N=\lambda*S_p*\rho_{liquid}$. The distance $\delta$ is the average distance of minimal approach between the protons of the non wetting liquid and the paramagnetic ions on the surface. S is the spin of the paramagnetic ions (S=5/2 for $Mn^{2+}$) in the solid. The unknown parameters in this model are $\eta_s$ the number of paramagnetic ions per gram of solid material, the length scale $\xi$, which correspond to the first layer of paramagnetic ions within the solid and the two correlation times $\tau_m$ and $\tau_s$.

Displayed in FIG. 1 are the calculated frequency dependences of proton spin-lattice relaxation rates for a translational diffusion correlation time $\tau_m=1$ ns and increasing values of the dynamical surface affinity parameter $A=\tau_s/\tau_m$ for 1 (corresponding to the relaxation with the bulk pore space), 3, 13, 130, 1300 and $\infty$ (corresponding to an unlimited surface area with a pure bilogarithmic NMRD relaxation features with a ratio of 10/3 between the low and high frequency slopes). When applying this method, the values found for this parameter will be useful to compare the surface affinity of oil in water-wet and oil-wet reservoirs. If $A=\tau_s/\tau_m$ goes to infinity the proton remains close to the wall without being trapped by paramagnetic. In this case, the fluid is strongly wetting to the surface.

The second model used in this example of the invention, also referred to as nuclear paramagnetic relaxation model, is based is based on the nuclear relaxation of a molecule trapped in a ligand field of a paramagnetic site. In case the proton spin-bearing molecule stays in the ligand field of the paramagnetic ions, the overall relaxation rate $1/T_1$ can be presented as a linear combination of a bulk and nuclear paramagnetic term:

$$\frac{1}{T_1(\omega_I, \omega_S)} = \frac{1}{T_{1bulk}} + \frac{N_{Param}}{N} \frac{1}{T_{1,param}(\omega_I, \omega_S)}, \quad [3]$$

where $N_{param}/N$ is the ratio of number of liquid molecules bonded to the paramagnetic molecule or sink at the surface and in the bulk, respectively.

Following the general theory of nuclear paramagnetic relaxation as documented for example in the original reference:

N. Bloembergen and L. O. Morgan, J. Chem. Phys. 34, 842 (1961) and the above references, the frequency dependency of the overall relaxation rate $1/T_1$ can be expressed as:

$$\frac{1}{T_1(\omega_I)} = \frac{1}{T_{1,bulk}} + \frac{2}{15}\lambda \varepsilon^2 S_P \rho_{liquid} \frac{(\eta_S \rho_{solid} \xi)}{\delta^6}(\gamma_I \gamma_S \hbar)^2 S(S+1)* \quad [4]$$

-continued $$T_{1,parameter}(\omega_S)\left[\frac{3}{1+\omega_I^2 T_{1,param}^2(\omega_S)} + \frac{7}{1+\omega_S^2 T_{1,param}^2(\omega_S)}\right],$$

where $\epsilon=0.3$ nm is the molecular size of water and $T_{1,param}$ is the electronic spin-lattice relaxation time (of the order of $10^{-11}$ s for the paramagnetic impurities).

Provided $1/T_{1,bulk}$ is known, the remaining undetermined parameters in this model are $\eta_s$, the number of paramagnetic ions per gram of solid material; the length scale $\xi$ which correspond to the first layer of paramagnetic ions within the solid; and the electronic spin-lattice relaxation time $T_{1,param}$.

Figure 2:
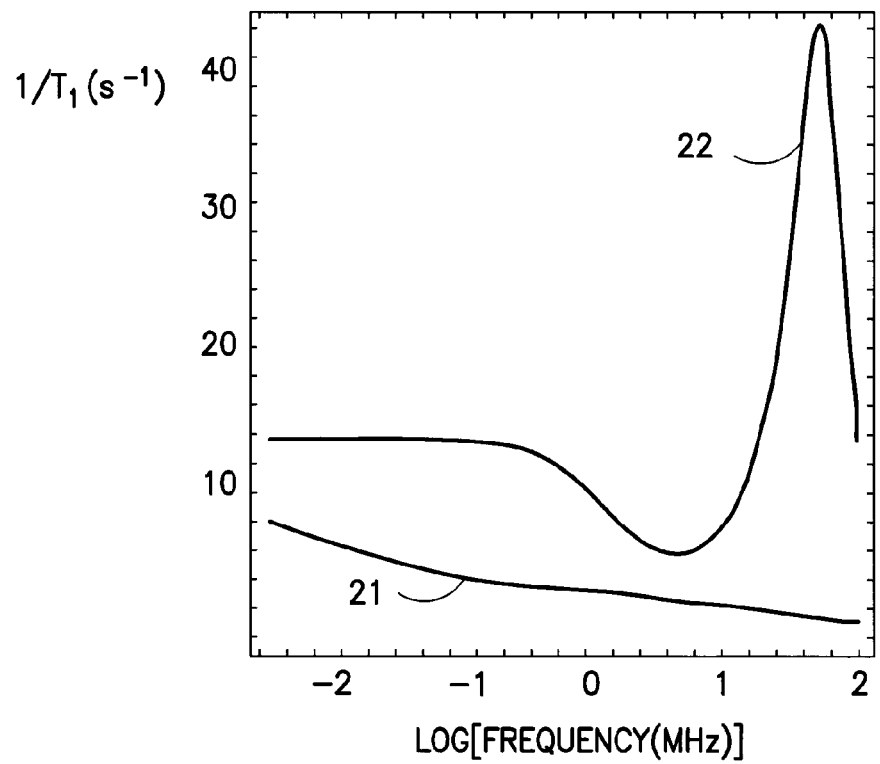
FIG. 2 shows two schematic plots of the frequency dependency of the relaxation rate $1/T_1$ for two different models of fluid behavior in the porous media in accordance with an example of the present invention.

The frequency dependency of the model represented by equation [4] is essentially flat at low frequencies and shows a characteristic peak at higher frequencies. Its typical shape is shown as curve 22 in FIG. 2. For comparison a typical curve for molecules described by the first model is shown as curve 21. The difference in the response of the molecules to the changing magnetic field as illustrated by the two curves 21, 22 is used in the present invention to determine wettability, the parameter A and other parameters as described below.

The following description and figures include examples of the novel methods and tools illustrating the application of the above derived models to determine wettability and further useful parameters. To further illustrate features of the invention based on measured data, samples of carbonate rock are investigated in a laboratory using a fast field cycling NMR spectrometer FFC commercially available from Steal s.r.l., Mede, Italy. The first sample A is a grainstone carbonate with 30% porosity and 700 mD permeability. The second sample B is a packstone carbonate with 11-12% porosity and 4-5 mD permeability.

To measure the proton relaxation rate $1/T_1$ spins were polarized at 15 MHz and free-induction decays were recorded following a single 90° excitation pulse of duration 5.8 s applied at 11 MHz. The temperature was fixed at 298 K. The experiment is repeated for a large range of Larmor frequency (10 kHz-20 MHz) to obtain the complete dispersion curve of $1/T_1$.

Figure 3:
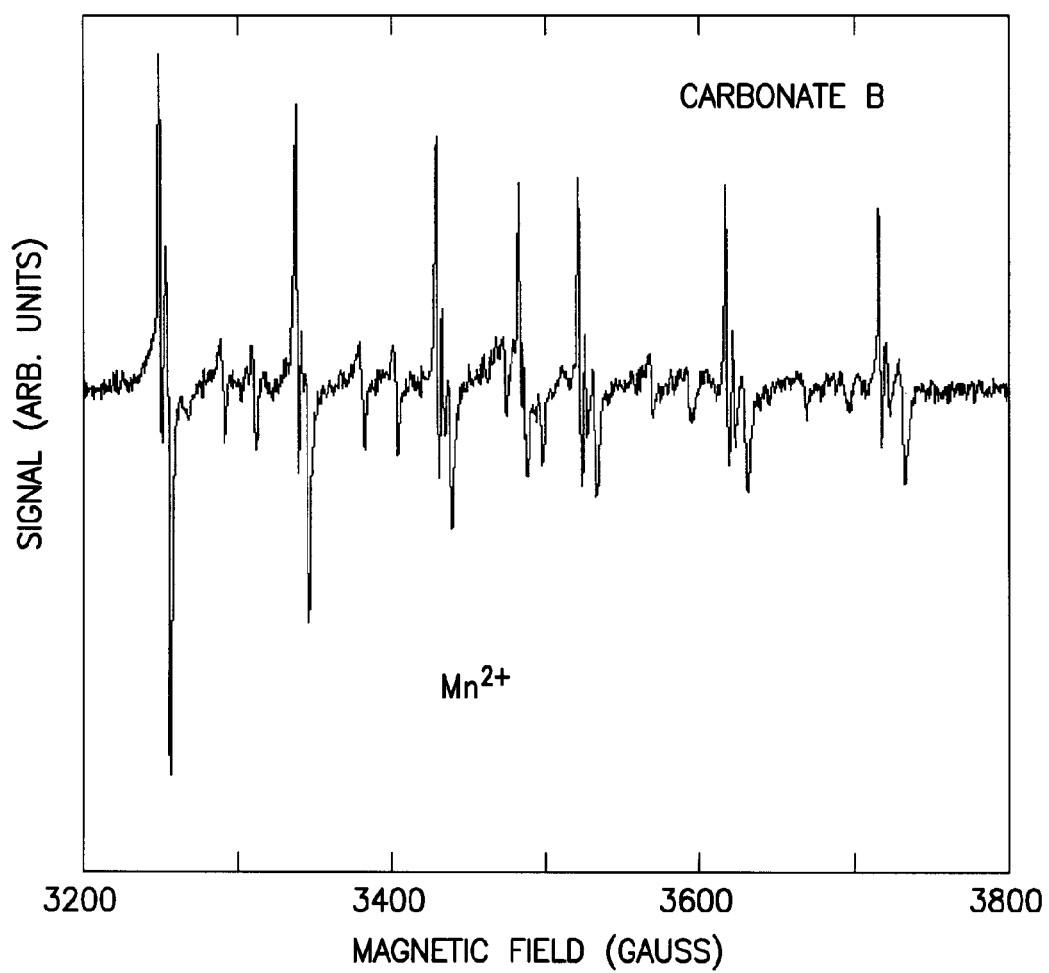
FIG. 3 shows an Electron Spin Resonance (ESR) spectrum measured at room temperature on a packstone carbonate sample.

In a first step, the exact amount of paramagnetic impurities in each sample is established. FIG. 3 shows a typical Electron Spin Resonance (ESR) spectrum measured at room temperature on a packstone carbonate (sample B, 11-12% porosity and 4-5 mD permeability). The six-peak hyperfine structure is typical of isolated $Mn^{2+}$ paramagnetic ions (S=5/2) convoluted by a powder pattern. Using a calibration of Electron Spin Resonance (ESR) spectrum based on a comparison of the ESR spectrum of some definite amounts of CuSO4 crystals diluted in KBr powders, the density of paramagnetic ions a re identified in FIG. 3 for sample B as $Mn^{2+}$ with electronic spin of S=5/2. The calibration method gives $\eta_s=3.3* 10^{17}$ ions per gram for sample B.

Figure 4A:
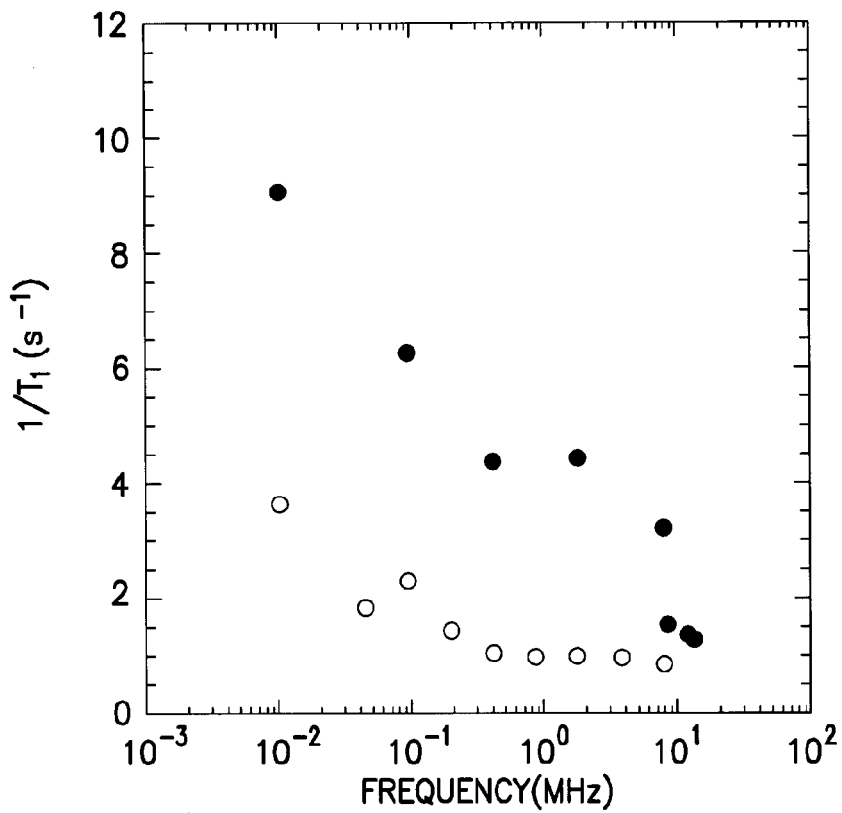
FIGS. 4A and 4B show the relaxation rate $1/T_1$ for Larmor frequencies in the range between 10 kHz-20 MHz of single phase saturations of dodecane in a first sample.
Figure 4B:
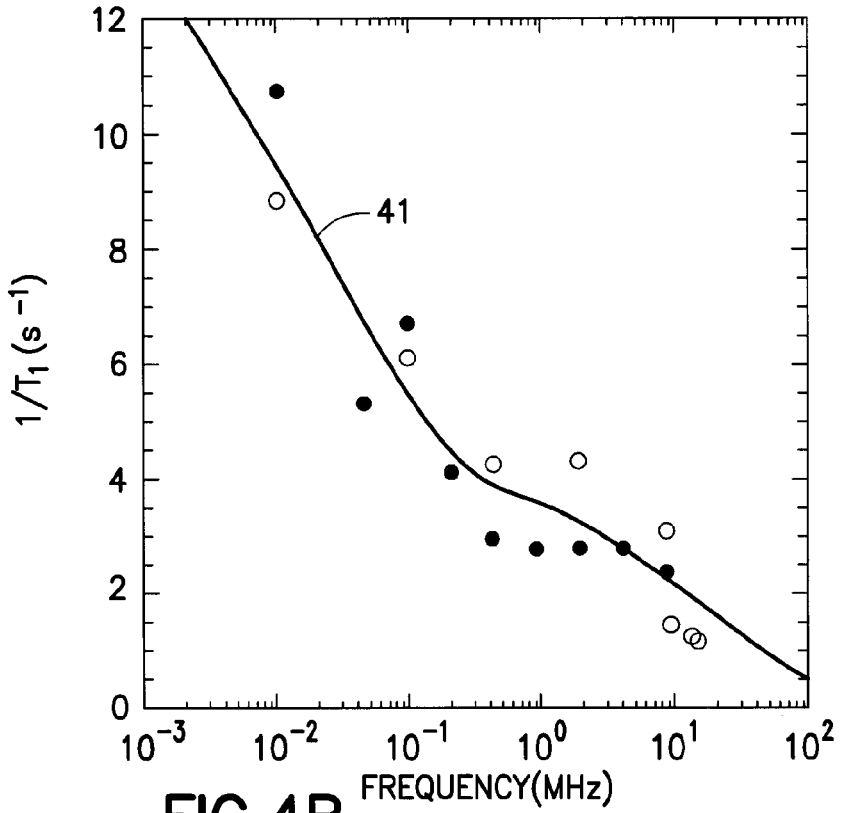

The proton relaxation rate $1/T_1$ NMRD for Larmor frequencies in the range between 10 kHz-20 MHz of single phase saturations of dodecane in sample B are shown in FIG. 4A. For each frequency, the biexponential decay of the longitudinal magnetization allows to find two spin-lattice relaxation rates labeled $R_{11}=1/T_{11}$ and $R_{12}=1/T_{12}$ in the FIG. 4c. However, both NMRD data follow the same nuclear paramagnetic relaxation model differing only by the presence of two dominant pore sizes in the rock sample. Thus, by choosing an appropriate scaling factor, the rescaled data can be represented by a single master NMRD curve 41 as shown in FIG. 4B.

This proves that a unique nuclear relaxation process is responsible for these NMRD features, namely the modulation of dipolar interaction by 2D translational diffusion of a non wetting liquid (equation [2]) that can be fitted with a translational diffusion correlation time $\tau_m=1.1$ ns and a surface residence time $\tau_s$ of 110 ns. It is interesting to note that these two parameters can be derived from the measurements without using all the parameters of the prefactor in equation [2]. The low value of the dynamical surface affinity $A=\tau_s/\tau_m=100$ supports the interpretation of dodecane as a non-wetting aprotic liquid.

Figure 4C:
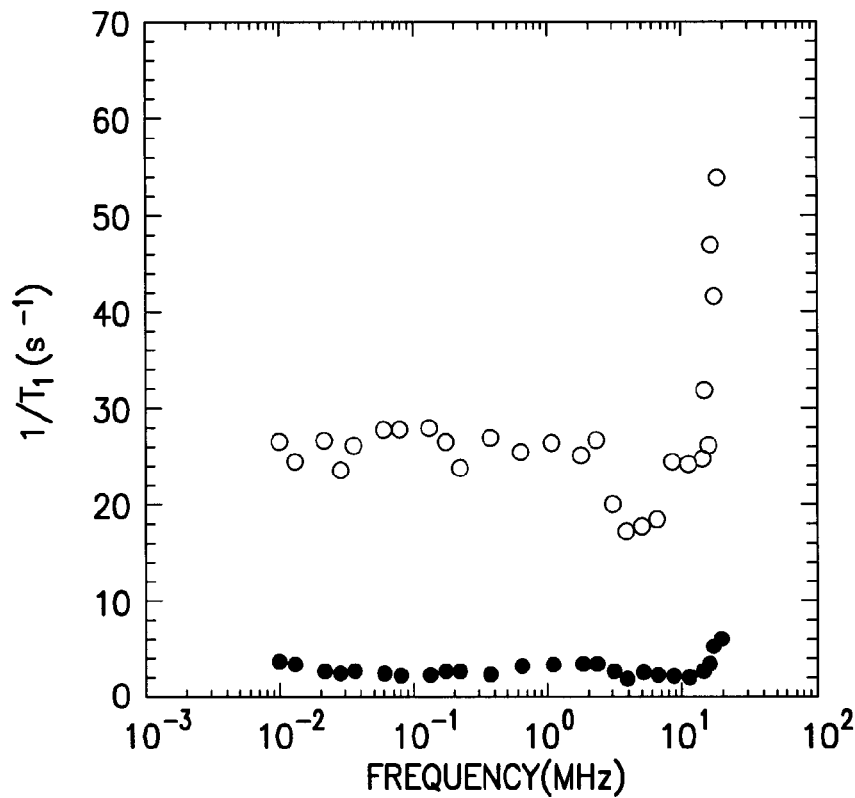
FIGS. 4C and 4D show the relaxation rate $1/T_1$ for Larmor frequencies in the range between 10 kHz-20 MHz of single phase saturations of brine in a second sample.
Figure 4D:
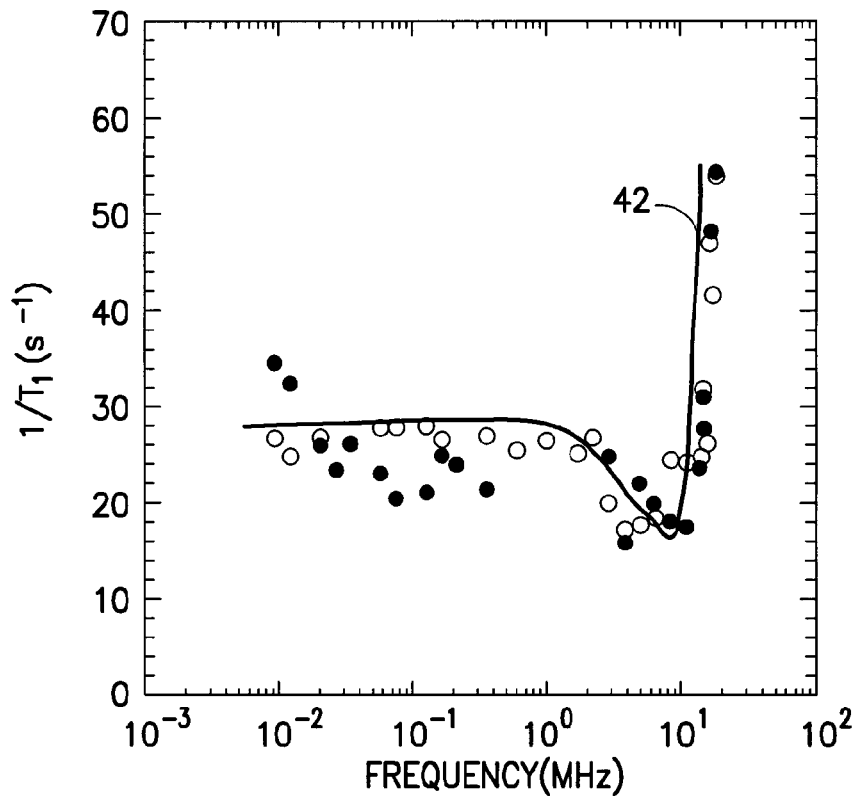

Similar measurements of brine in sample A are shown in FIG. 4C. Again the measurements show two different relaxation rates. However, as with dodecane above using equation [4] and rescaling the two sets or data can be combined and represented by a single master NMRD curve 42 as shown in FIG. 4D. This rescaling proves again that a unique nuclear relaxation process is responsible for these NMRD features, namely the nuclear paramagnetic relaxation. So, the data for brine in sample A behave in accordance with the model for a wetting liquid as developed above in equation [4] when fitted with an electronic spin-lattice relaxation time $T_{1,param}=8.6 \ 10^{-11}$ s.

Figure 5:
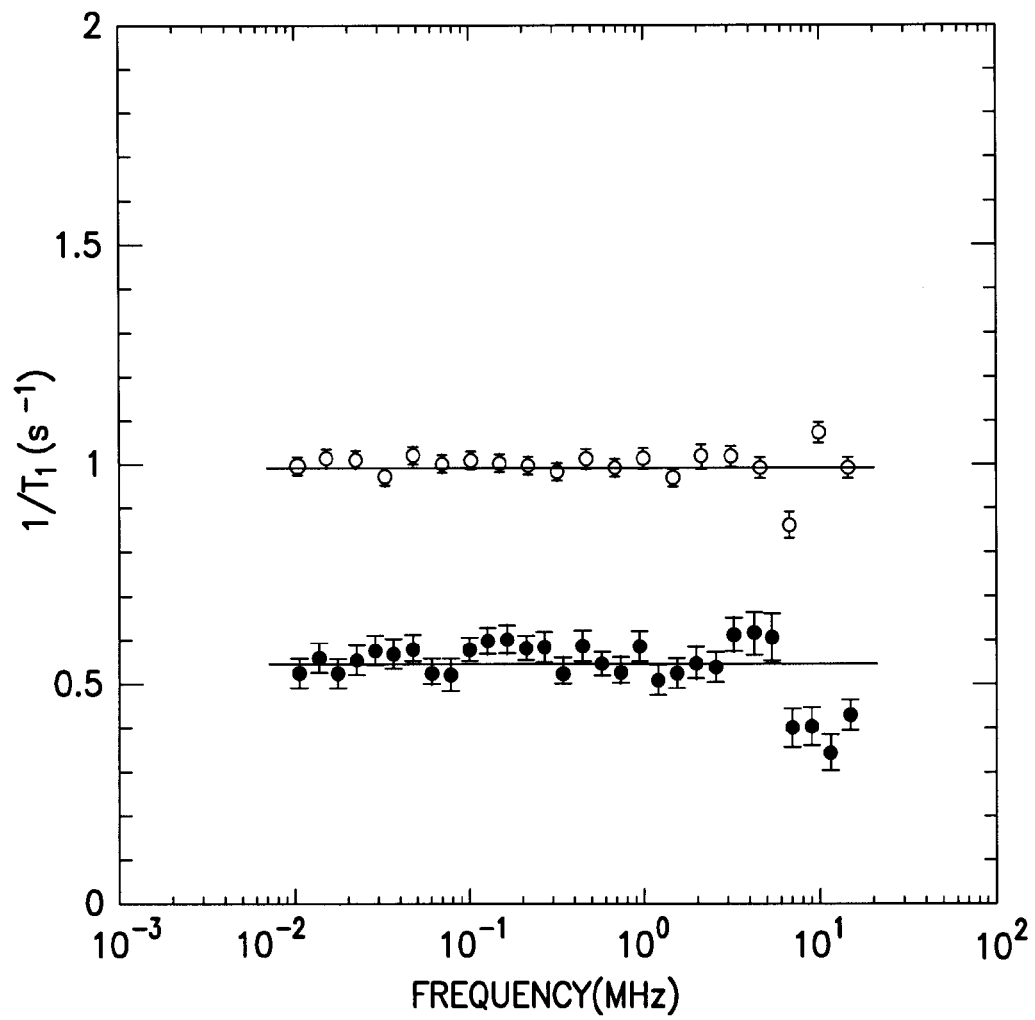
FIG. 5 shows NMRD data of bulk brine and dodecane for Larmor frequencies in the range between 10 kHz-20 MHz.

In FIG. 5, measured proton spin-lattice relaxation rates as function of the magnetic field strength are plotted as a function of the proton Larmor frequency for bulk dodecane and brine (water with 50 000 ppm NaCl) at 298 K. The relaxation rates for the bulk fluids are essentially constant over the range of frequencies with $1/T_{1b,water}=0.55$ s$^{-1}$ and $1/T_{1b,dodecane}=1.0$ s$^{-1}$, respectively.

Figure 6:
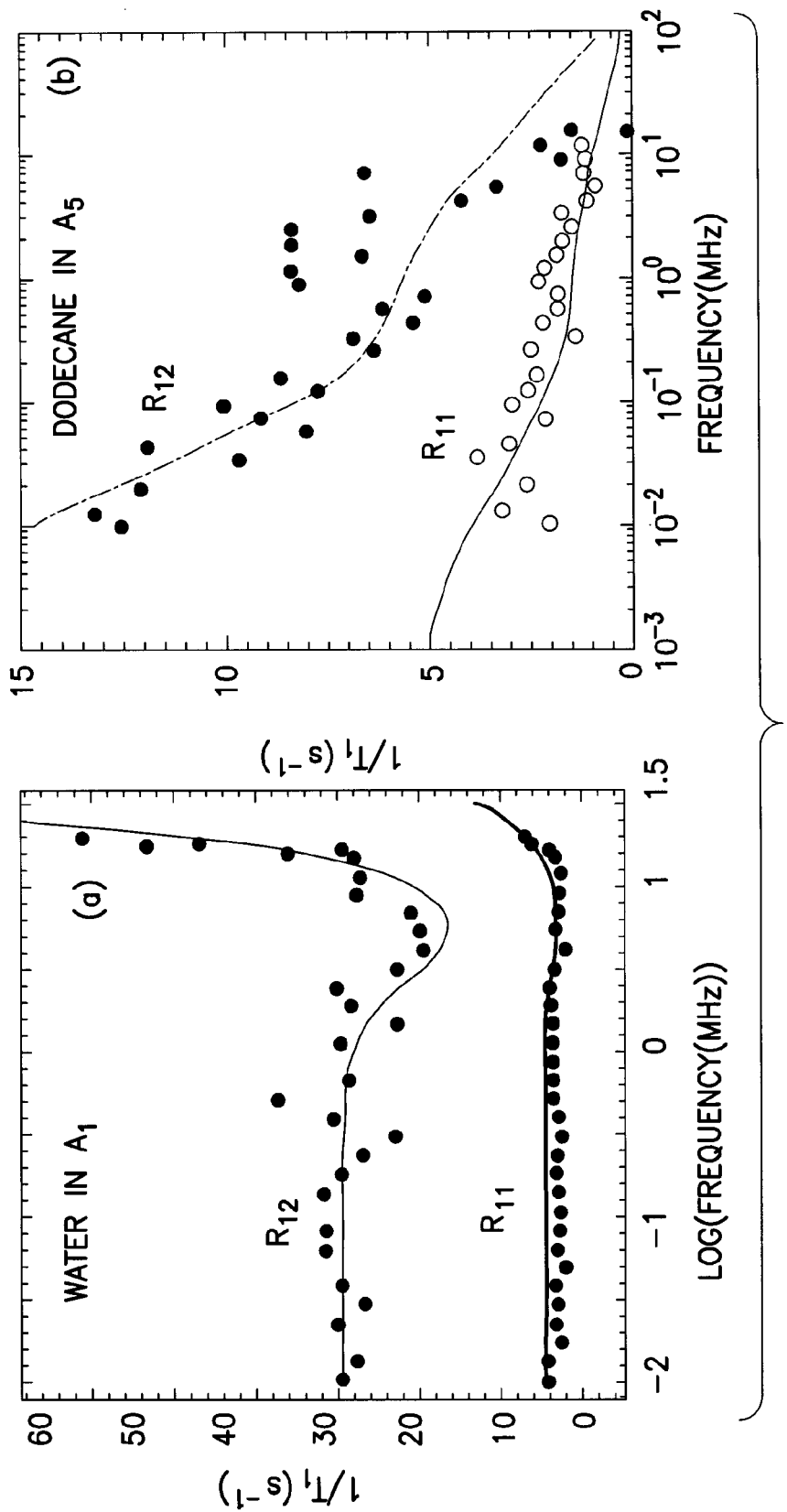
FIGS. 6a and 6b show measured proton spin-lattice relaxation rates as function of the magnetic field strength plotted as the proton Larmor frequency, for (a) brine and (b) dodecane, saturating a grainstone carbonate (30% porosity, 700 mD permeability) at 298 K.
Figure 7:
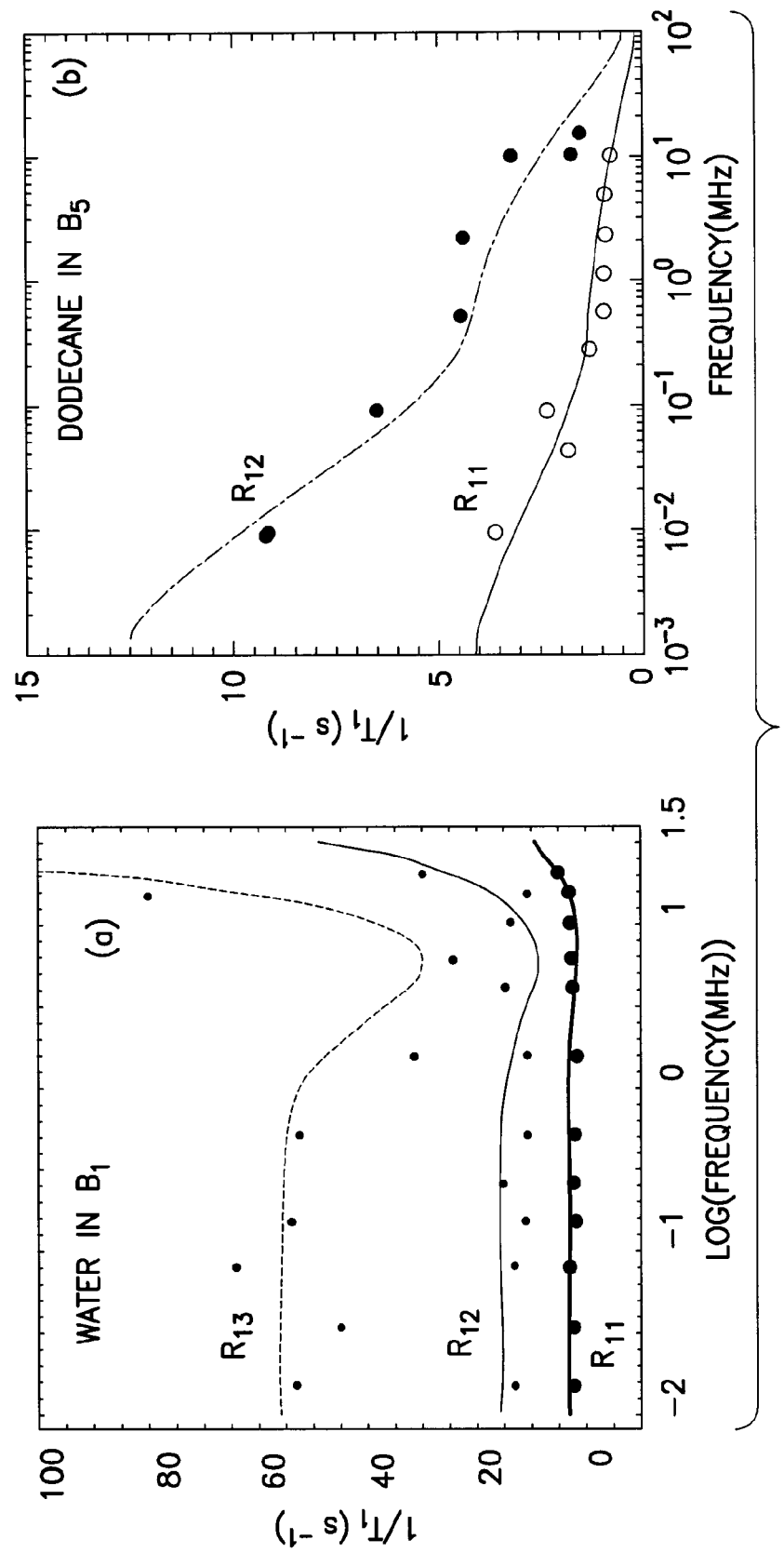
FIGS. 7a and 7b show measured proton spin-lattice relaxation rates as function of the magnetic field strength plotted as the proton Larmor frequency, for (a) brine and (b) dodecane, saturating a packstone carbonate (11-12% porosity, 4-5 mD permeability) at 298 K.

FIGS. 6 and 7 show all the results for monophasic saturations of water-brine (a) and dodecane (b) in carbonate samples A and B, respectively. FIGS. 6a, b) show measured proton spin-lattice relaxation rates as function of the magnetic field strength plotted as the proton Larmor frequency, for (a) brine and (b) dodecane, saturating a grainstone carbonate (30% porosity, 700 mD permeability) at 298 K. The continuous lines have been obtained from Eq. (2) for the non wetting dodecane (b) and from Eq. (4) for the wetting water (a).

FIGS. 7a, b) show measured proton spin-lattice relaxation rates as function of the magnetic field strength plotted as the proton Larmor frequency, for (a) brine and (b) dodecane, saturating a packstone carbonate (11-12% porosity, 4-5 mD permeability) at 298 K. Here $R_{11}=1/T_{11}$, $R_{12}=1/T_{12}$ and $R_{13}=1/T_{13}$ represent the three spin-lattice relaxation rates obtained from a triexponential decay of the longitudinal magnetization. The continuous lines have been obtained from Eq. (2) for the non wetting dodecane (b) and from Eq (4) for the wetting water (a).

In FIGS. 6 and 7 the fits have been obtained using the correlation times deduced from the rescaling procedure described above however using all parameters including the static parameters of the equations [2] and [4]. The figures demonstrate the influence of the different formation parameters of rock samples A and B on relaxation rates. For instance, in rock sample B saturated only by brine (FIG. 7a), a tri-exponential magnetization decay can be identified, contrary to the case of a saturation with dodecane (FIG. 7b). The wetting character of water in this rock reveals new information about the complexity of the porosity of this carbonate rock, not visible by the results obtained from the non-wetting dodecane.

Figure 8A:
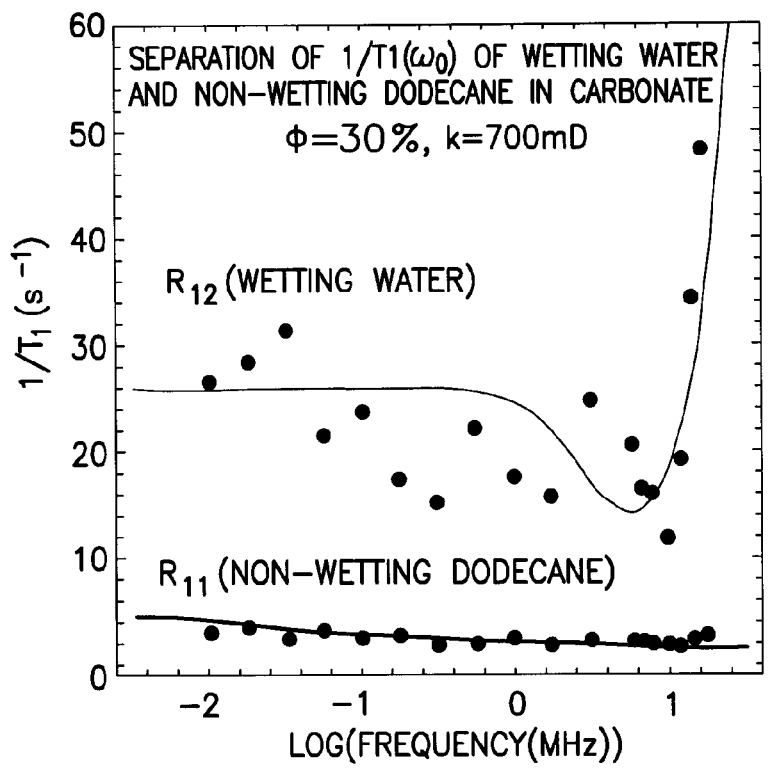
FIG. 8A shows the NMRD data in the case of a biphasic saturation of water-brine and dodecane in a rock sample when irreductible saturation of water is reached.

FIG. 8A shows the NMRD data in the case of a biphasic saturation of water-brine and dodecane in sample A at 298 K. The rock sample is first 100% saturated with brine, then centrifuged by dodecane until the irreducible saturation of water is reached. The continuous lines have been obtained using eq. [2] for the non wetting dodecane and eq. [4] for the wetting water. The result shows that the water has been trapped in the ligand field of the paramagnetic sites and therefore wets the rock surface. Similarly, the data show that the surface affinity of dodecane is low (A=100).

Figure 8B:
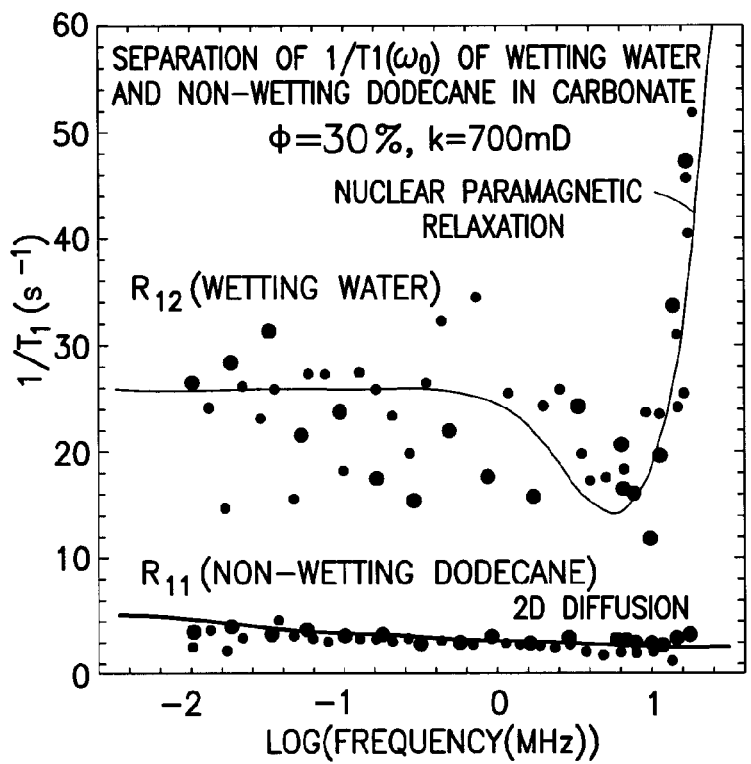
FIG. 8B shows the NMRD data of FIG. 5A overlayed onto measured for monophasic saturations.

FIG. 8B show the relaxation rates of the mixture (large full dots) as shown in FIG. 8A overlayed with the rates $R_{11}=1/T_{11}$ and $R_{12}=1/T_{12}$ (small dots) as obtained for monophasic saturations of dodecane and water, respectively, in sample A. These data show that water is confined in the smallest pores (largest rates $R_{12}$) and dodecane is confined in the largest pores (smallest rates $R_{11}$).

Figure 8C:
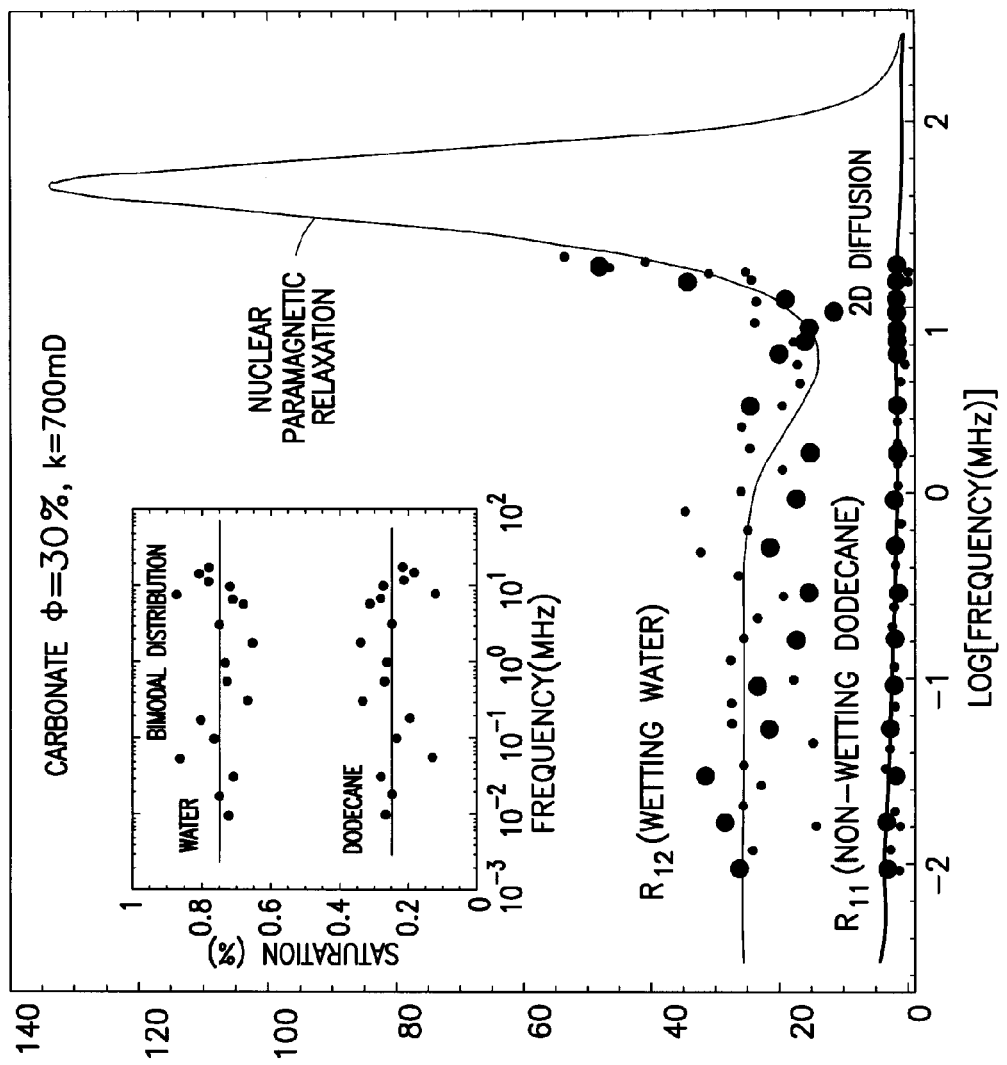
FIG. 8C shows the data of FIG. 8B in an extended frequency range together with an inset showing the saturation (%) of water and dodecane obtained when irreductible saturation of water is reached.

FIG. 8C shows data of the same setup as FIG. 8B, but here the range of frequency has been extended to exhibit the different theoretical relaxation features of the nuclear paramagnetic relaxation model and the two-dimensional diffusive relaxation model. Moreover, the inset in the figure show the saturation (%) of water and dodecane obtained when irreducible saturation of water is reached. This inset demonstrates that methods in accordance with the invention can also be used to determine the saturation of a fluid in a porous medium. Thus, FIG. 8C illustrates that the proposed method allows determining relative saturation of fluid phases as a function of pore size, and wettability of each fluid as a function of pore size as well.

It will be understood that processing can be performed downhole and/or uphole, and that some of the processing may be performed at a remote location. The new methods and tools in accordance with the present invention can be used either in laboratories on core samples or in-situ, i.e., directly in a wellbore using the formation rock as sample. Also, while a wireline tool is illustrated below, alternative forms of physical support and communicating link can be used, for example in a measurement while drilling system.

The frequency dependent NMR $T_1$ signal can be obtained in the laboratory using for instance a Field Cycling NMR relaxometer. The proposed methodology can be applied for laboratory measurement on cores, either preserved cores, or artificially saturated with various fluids, for instance wettability modifiers or any chemical additive to be controlled with respect to wettability. The measurements on cores can be used for calibration purpose with the aim to carry out quantitative measurements with a logging tool.

In in-situ application the frequency dependent NMR $T_1$ signal can be obtained in a well, using for instance the commercially available MR Scanner (TM of Schlumberger) or an equivalent tool. The MR Scanner is capable of measuring $T_1$ distributions in the range of 0.5 to 2 Mhz and diffusion (D)-$T_2$plots. The frequencies correspond to different radial depth shells around the wellbore, as described for example in the document SPE 84482 "A next generation wireline NMR logging tool by DePavia et al.

As the $T_1$ signals are obtained from different depth shells, the saturations of the formation fluids at these location may vary thus causing an error when applying the methods describe above. To reduce or eliminate this potential source of error from the measurement, the radial depth shells with essentially uniform saturations are selected and only $T_1$ measurements from the selected depth shells are consider for the modeling. The radial depth shells with uniform saturations can be identified using for example the D-$T_2$ plots provided by the same tool. This procedure allows plotting the affinity parameter A at each logging position resulting in wettability as the function of logging depth.

What is claimed is:

1. A method of determining wettability of a fluid embedded in a porous medium, by means of nuclear magnetic relaxation dispersion measurements, said method comprising the steps of:
   measuring values of the spin-lattice relaxation $T_1$ time of the fluid in the porous medium using a nuclear magnetic resonance (NMR) tool at varying nuclear Larmor frequencies by means of inversion recovery, or a spin-echo pulse sequence, or a derivative thereof;
   deriving a dispersion curve of the measured values of the spin-lattice relaxation $T_1$ time at varying Larmor frequencies;
   the method being characterized by determining whether the dispersion curve is essentially flat at low frequencies and shows a peak at higher frequencies characteristic of a wetting fluid embedded in the porous media or a bilogarithmic frequency dispersion characteristic of a non-wetting fluid embedded in the porous media;
   using the dispersion curve to separate quantitatively the fluid; and
   wherein the step of using the dispersion curve to separate quantitatively the fluid leads to a pore size dependence of the wettability.

2. The method of claim 1, wherein the porous medium is a rock sample.

3. The method of claim 1, further comprising determining a wettability index of the fluid using the ratio of a surface residence time $\tau_s$ and a translational diffusion correlation time $\tau_m$.

4. The method of claim 1, further comprising using an electronic spin-lattice relaxation time to determine the amount of paramagnetic impurities in the porous medium ηs, and using the amount of paramagnetic impurities ηs to determine the dispersion curve of the fluid.

5. The method of claim 1, wherein the nuclear magnetic resonance (NMR) tool is a logging tool.

6. The method of claim 1 wherein the nuclear Larmor frequencies are from 10 kHz to 20 Mhz.

7. The method of claim 1 wherein the fluid is a mixture of oil and brine.

8. The method of claim 1 further comprising: deriving information related to pore size distribution from the dispersion curve.

9. The method of claim 1 further comprising: determining a saturation of the fluid in the porous media.

* * * * *